US012599355B2

(12) United States Patent (10) Patent No.: US 12,599,355 B2
Xu et al. (45) Date of Patent: Apr. 14, 2026

(54) STETHOSCOPE KIT

(71) Applicant: BINJIANG INSTITUTE OF ZHEJIANG UNIVERSITY, Hangzhou (CN)

(72) Inventors: Weize Xu, Hangzhou (CN); Qiang Shu, Hangzhou (CN)

(73) Assignee: BINJIANG INSTITUTE OF ZHEJIANG UNIVERSITY, Hangzhou (CN)

( * ) Notice: Subject to any disclaimer, the term of this patent is extended or adjusted under 35 U.S.C. 154(b) by 379 days.

(21) Appl. No.: 18/494,517

(22) Filed: Oct. 25, 2023

(65) Prior Publication Data

US 2024/0148354 A1     May 9, 2024

Related U.S. Application Data

(63) Continuation of application No. PCT/CN2022/118592, filed on Sep. 14, 2022.

(30) Foreign Application Priority Data

Nov. 18, 2021    (CN) .......................... 202111370217.8

(51) Int. Cl.
*A61B 7/04*             (2006.01)

(52) U.S. Cl.
CPC ........ *A61B 7/04* (2013.01); *A61B 2562/0204* (2013.01)

(58) Field of Classification Search
CPC .......................... A61B 7/04; A61B 2562/0204
See application file for complete search history.

(56) References Cited

U.S. PATENT DOCUMENTS 9,265,478 B2 * 2/2016 Wang ........................ A61B 7/04
10,709,414 B1 * 7/2020 McLane .................. G16H 40/63
2013/0096539 A1 * 4/2013 Wood ...................... H02J 7/485
606/1

* cited by examiner

*Primary Examiner* — Tse W Chen
*Assistant Examiner* — Joseph A Tombers

(57) ABSTRACT

A stethoscope kit includes a storage cylinder, a protective shell and an electronic stethoscope. The storage cylinder includes a base and a cylinder body. The protective shell is configured to be sleeved on the cylinder body. Two sides of the cylinder body are each symmetrically provided with a groove. A bottom of the groove is provided with an accommodating groove configured to accommodate the electronic stethoscope. A bottom of the accommodating groove is attached to a bottom of the electronic stethoscope through an attraction mechanism. A charging device is provided in the cylinder body. When the electronic stethoscope is placed in the accommodating groove, the charging device is configured to charge the electronic stethoscope.

6 Claims, 9 Drawing Sheets

45

51

STETHOSCOPE KIT

CROSS-REFERENCE TO RELATED APPLICATIONS

This application is a continuation of International Patent Application No. PCT/CN2022/118592, filed on Sep. 14, 2022, which claims the benefit of priority from Chinese Patent Application No. 202111370217.8, filed on Nov. 18, 2021. The content of the aforementioned application, including any intervening amendments thereto, is incorporated herein by reference in its entirety.

TECHNICAL FIELD

This application relates to medical appliances, and more particularly to a stethoscope kit.

BACKGROUND

With the development of science and technology, the stethoscope has gradually evolved from the traditional stethoscope composed of a chestpiece, a flexible tubing and earpieces to the electronic stethoscope. The existing electronic stethoscopes are free of the tubing and the earpieces, and instead, a wireless transmission device is set in the stethoscope body for connection with the terminal devices, such as the mobile phone, so as to enable the transmission of the detected sound.

SUMMARY

Generally, about two stethoscopes are required at home, and four or more stethoscopes are needed in the hospital. Considering that the electronic stethoscopes are in one-to-one matching with storage boxes, it fails to enable the centralized storage of the electronic stethoscopes, thereby increasing the management difficulty.

In view of problems in the prior art, this application provides a stethoscope kit.

Technical solutions of the present disclosure will be described as follows.

This application provides a stethoscope kit, comprising:
a storage cylinder;
a protective shell; and
an electronic stethoscope;
wherein the storage cylinder comprises a base and a cylinder body; the protective shell is adapted to be sleeved on the cylinder body; two sides of the cylinder body are each symmetrically provided with a recess; a bottom of the recess is provided with an accommodating groove to accommodate the electronic stethoscope; a bottom of the electronic stethoscope is attached to a bottom of the accommodating groove through an attraction mechanism; a charging device is provided in the cylinder body; the charging device is configured to charge the electronic stethoscope when the electronic stethoscope is placed in the accommodating groove.

The working principle of the present disclosure is explained as follows. Regarding the stethoscope kit designed herein, the number of accommodating grooves can be set to meet the requirements of different application scenarios. For household use, recessed at the two sides of the cylinder body are each provided with one accommodating groove. For hospital, the recesses at the two sides of the cylinder body are each provided with two or three accommodating grooves. When the stethoscope is needed to use, the protective shell is removed from the cylinder body, and then the electronic stethoscope can be taken away. After use, the electronic stethoscope is returned to the accommodating groove, and the charging device will charge the electronic stethoscope. And then the protective shell is sleeved on the cylinder body. In summary, the stethoscope kit of the present disclosure is very convenient and practical.

In an embodiment, the charging device comprises a charging wire and a plurality of engagement devices; the charging wire is provided on the base; the plurality of engagement devices are in one-to-one correspondence with the accommodating grooves; each of the plurality of engagement devices comprises a first drive motor, a running channel, a rack and an engagement part; the running channel comprises a first channel and a second channel; an accommodating cavity is provided in the cylinder body; a first end of the first channel is communicated with the accommodating cavity, and a second end of the first channel is communicated with the second channel; the second channel is arranged around a side wall of the accommodating groove, and the side wall of the accommodating groove is provided with an opening communicated with the second channel; the engagement part is electrically connected with the charging wire; the engagement part is provided on an end of the rack; a side wall of the electronic stethoscope is provided with an engagement block; a side wall of the engagement block is provided with an engagement groove configured insertion of the engagement part; the first drive motor is provided on a side of the accommodating cavity; an output shaft of the first drive motor is provided with a drive gear configured to be engaged with the rack; the first drive motor is configured to drive the rack to move along the running channel; and the engagement part is located in the first channel in a non-operation state.

In an embodiment, an interior of the cylinder body is provided with a first control device configured to control the first drive motor; the bottom of the accommodating groove is provided with a pressure sensor, and the pressure sensor is configured to sense pressure change to determine whether the electronic stethoscope is placed in the accommodating groove.

In an embodiment, the electronic stethoscope comprises a case, a microphone and a second control device; the microphone and the second control device are provided in the case; the second control device is provided with a wireless transmission device; a top of the case is provided with a start switch; a sound-receiving end of the microphone extends out of a bottom of the case; the top of the case is provided with a mounting groove; a bottom of the mounting groove is provided with a light-emitting diode (LED); and the mounting groove is filled with a transparent filling block.

In an embodiment, the attraction mechanism comprises a first magnet group and a second magnet group; the first magnet group comprises a plurality of first magnets, and the second magnet group comprises a plurality of second magnets; the first magnet group is provided on the bottom of the accommodating groove; the plurality of first magnets are evenly distributed along a circumference of the accommodating groove; the bottom of the case is provided with an embedding groove configured for embedding of the plurality of first magnets; and the plurality of second magnets are evenly distributed along a circumference of the embedding groove.

In an embodiment, a side of the base is provided with a slot; a cavity is provided in the base; a wire winding device is provided in the cavity; the slot is communicated with the cavity of the case; the wire winding device comprises a second drive motor and a wire winding reel; the charging wire comprises a plug and a conductive wire; the slot is configured to accommodate the plug; the second drive motor is configured to drive the wire winding reel to rotate, so as to wind the wire; and a side wall of the base is provided with a control button, and the control button is configured to control operation of the second drive motor.

In an embodiment, the base is provided with an insertion slot around the cylinder body; and a bottom of the protective shell is provided with a protrusion configured to be inserted into the insertion slot.

In an embodiment, a top of the protective shell is provided with a hole.

Compared to the prior art, the present disclosure has an advantage of convenient centralized storage of the electronic stethoscope.

Figure 1:
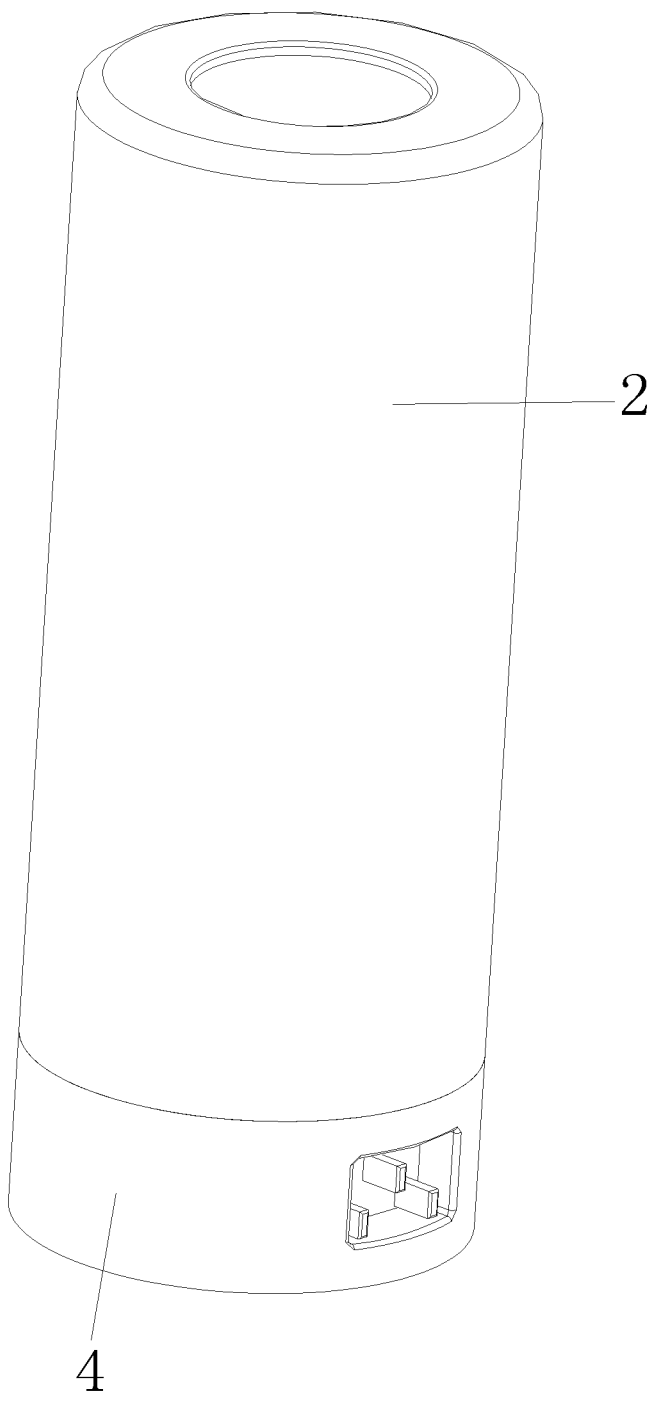
FIG. 1 schematically shows a structure of a stethoscope kit according to an embodiment of the present disclosure.

In the figures: storage cylinder 1; protective shell 2; electronic stethoscope 3; base 4; cylinder body 5; recess 6; accommodating groove 7; charging device 9; charging wire 11; first drive motor 13; running channel 14; rack 15; engagement part 16; first channel 17; second channel 18; accommodating cavity 19; opening 20; drive gear 21; first control device 22; pressure sensor 23; case 24; microphone 25; second control device 26; wireless transmission device 27; start switch 28; sound-receiving end 29; mounting groove 30; light-emitting diode 31; filling block 32; first magnet group 33; second magnet group 34; magnet 35; slot 37; cavity 38; wire winding device 39; second drive motor 40; plug 42; conductive wire 43; wire winding reel 44; insertion slot 45; protrusion 46; hole 47; rubber ring 48; engagement block 49; engagement groove 50; and control button 51.

DETAILED DESCRIPTION OF EMBODIMENTS

The present disclosure will be further described below with reference to the accompanying drawings and embodiments, and the embodiments described herein are only to illustrate this application rather than limiting this application.

Figure 2:
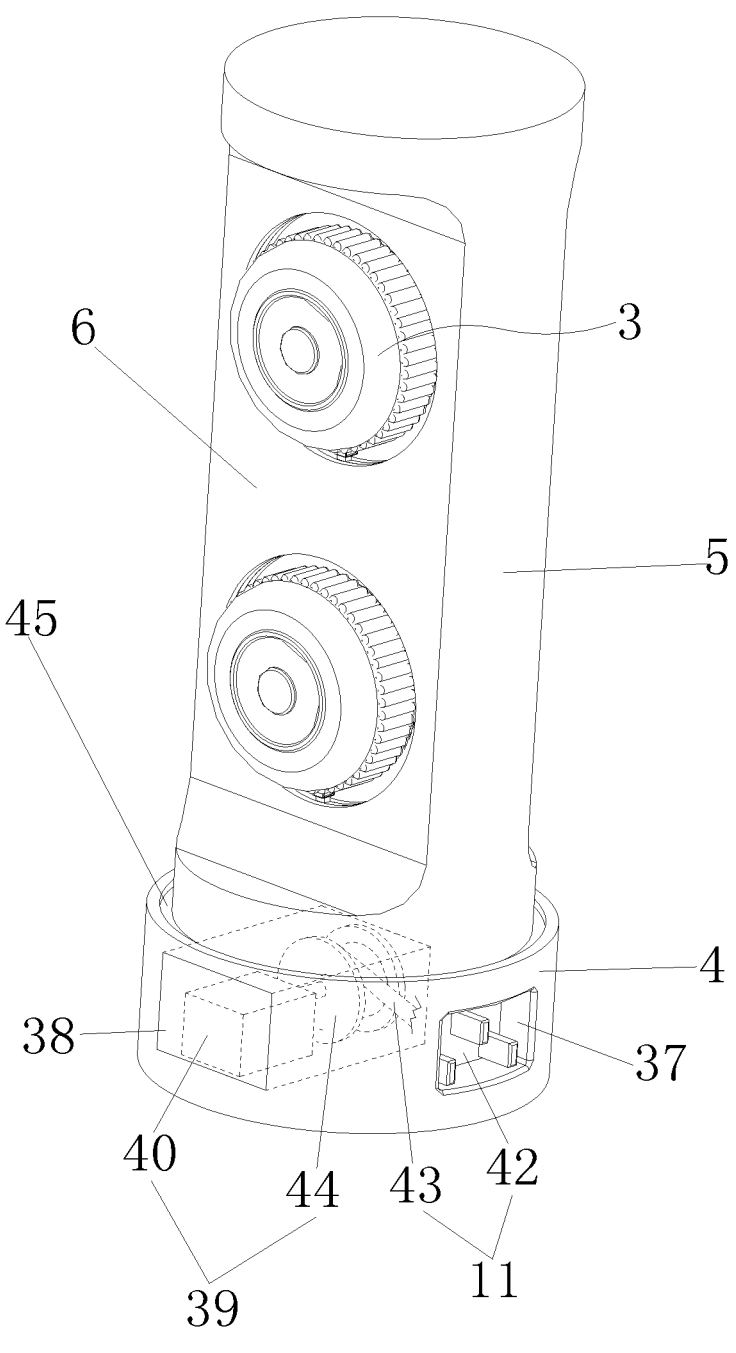
FIG. 2 schematically shows a structure of a storage cylinder according to an embodiment of the present disclosure.
Figure 3:
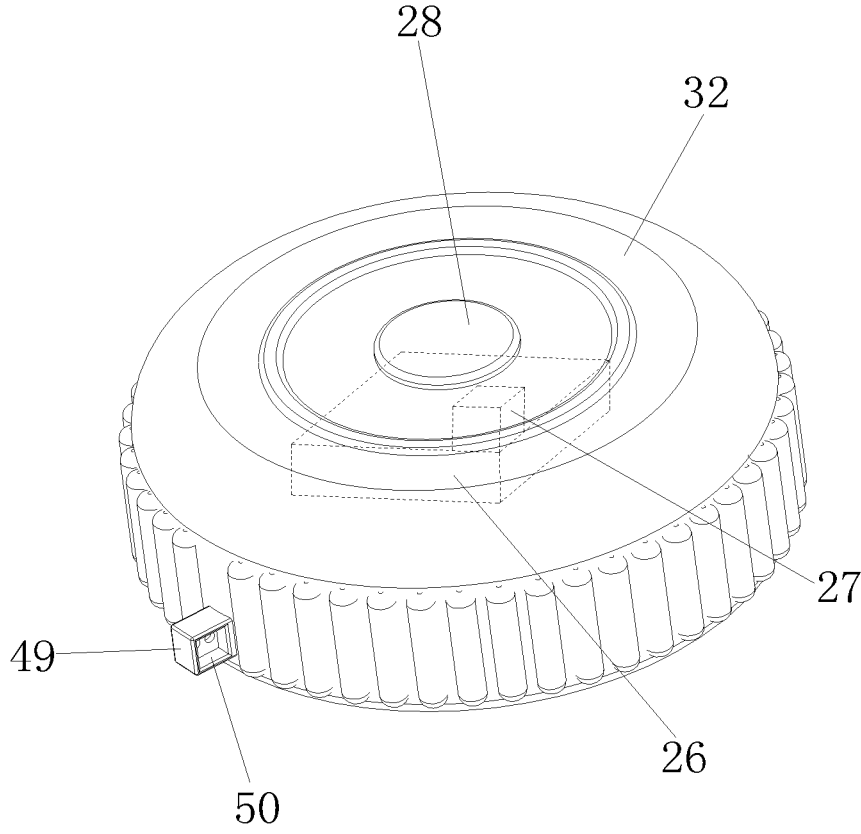
FIG. 3 schematically shows a structure of an electronic stethoscope according to an embodiment of the present disclosure.
Figure 4:
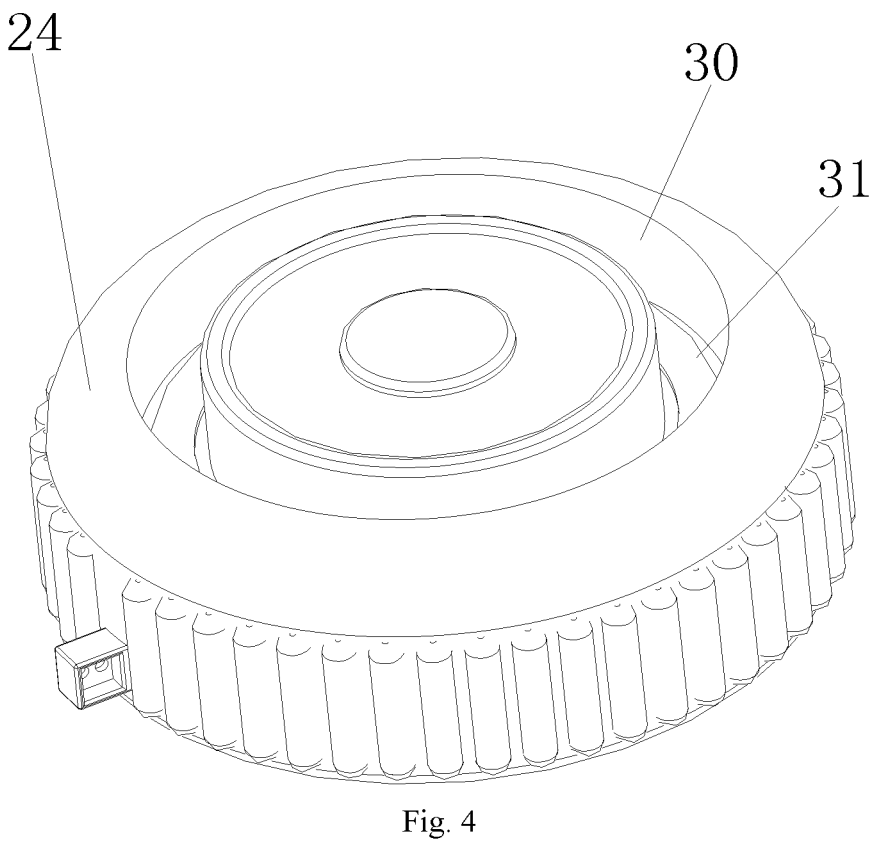
FIG. 4 schematically shows a structure of the electronic stethoscope without a transparent filling block according to an embodiment of the present disclosure.
Figure 5:
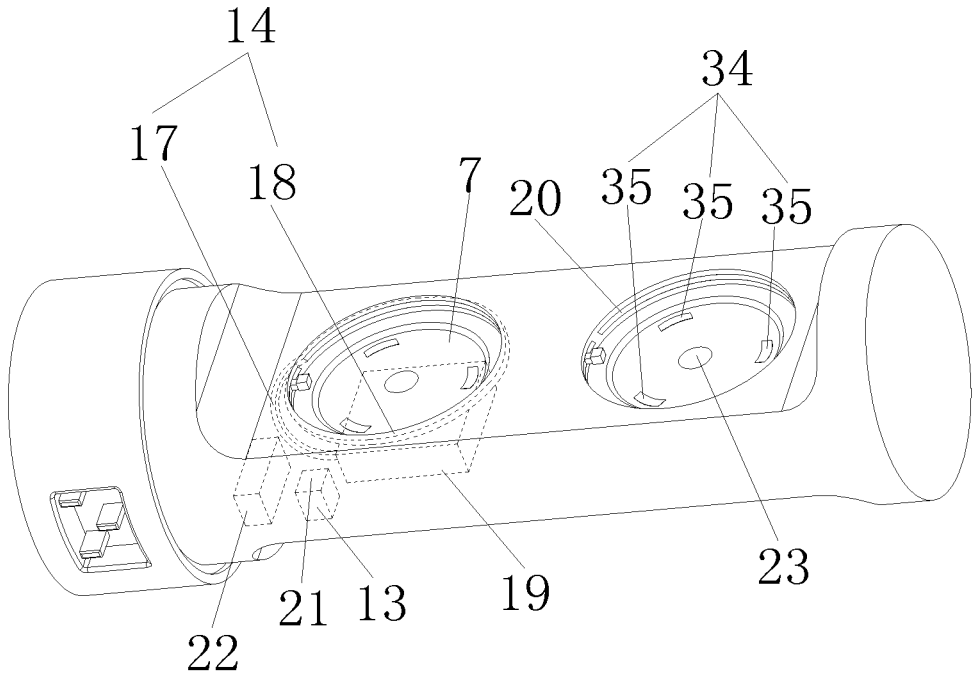
FIG. 5 schematically shows the structure of the storage cylinder according to an embodiment of the present disclosure.
Figure 6:
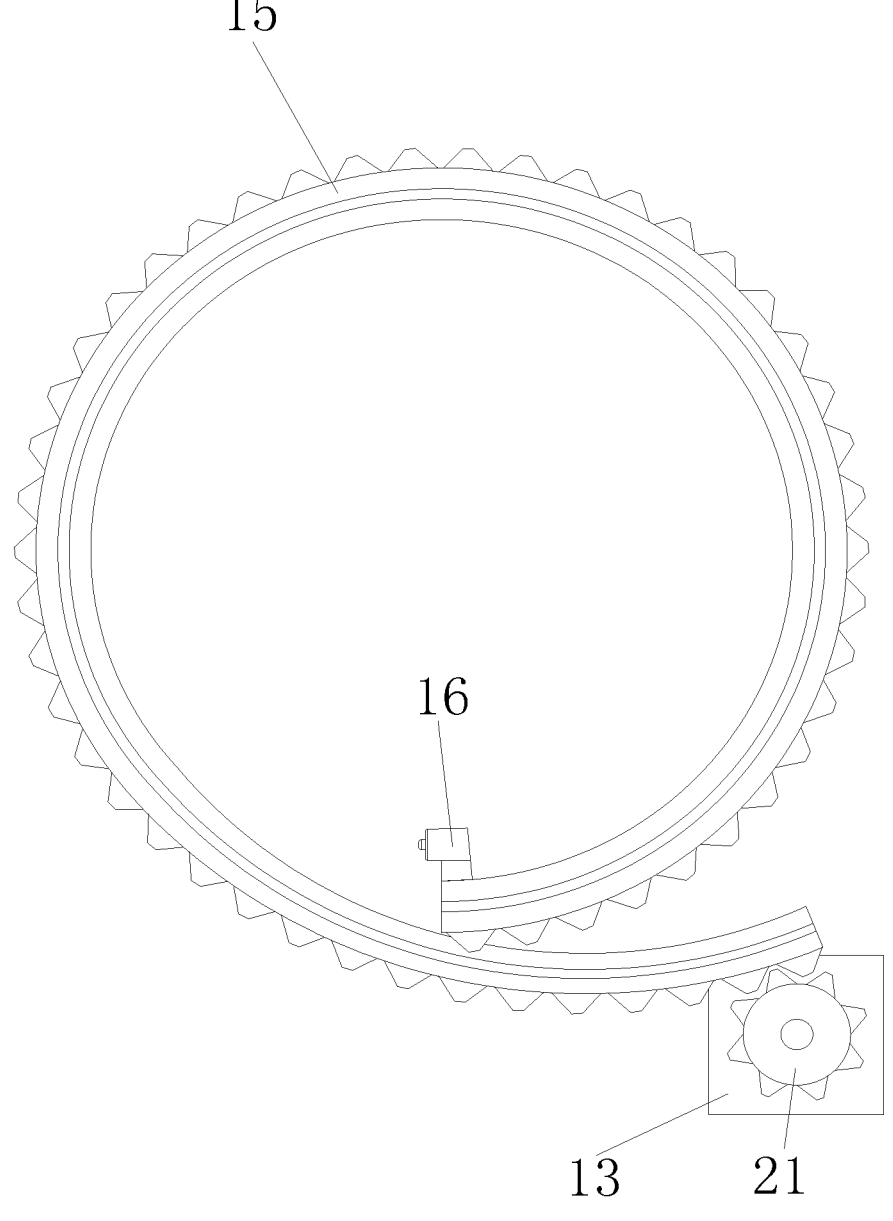
FIG. 6 schematically shows a structure of a rack according to an embodiment of the present disclosure.
Figure 7:
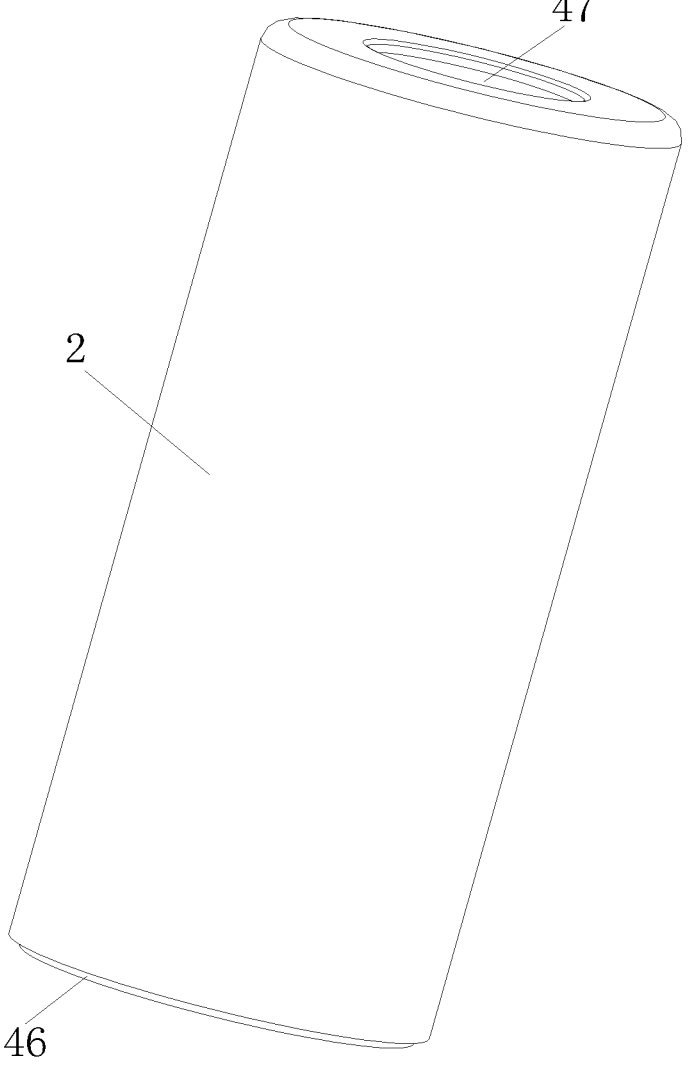
FIG. 7 schematically shows a structure of a protective shell according to an embodiment of the present disclosure.
Figure 8:
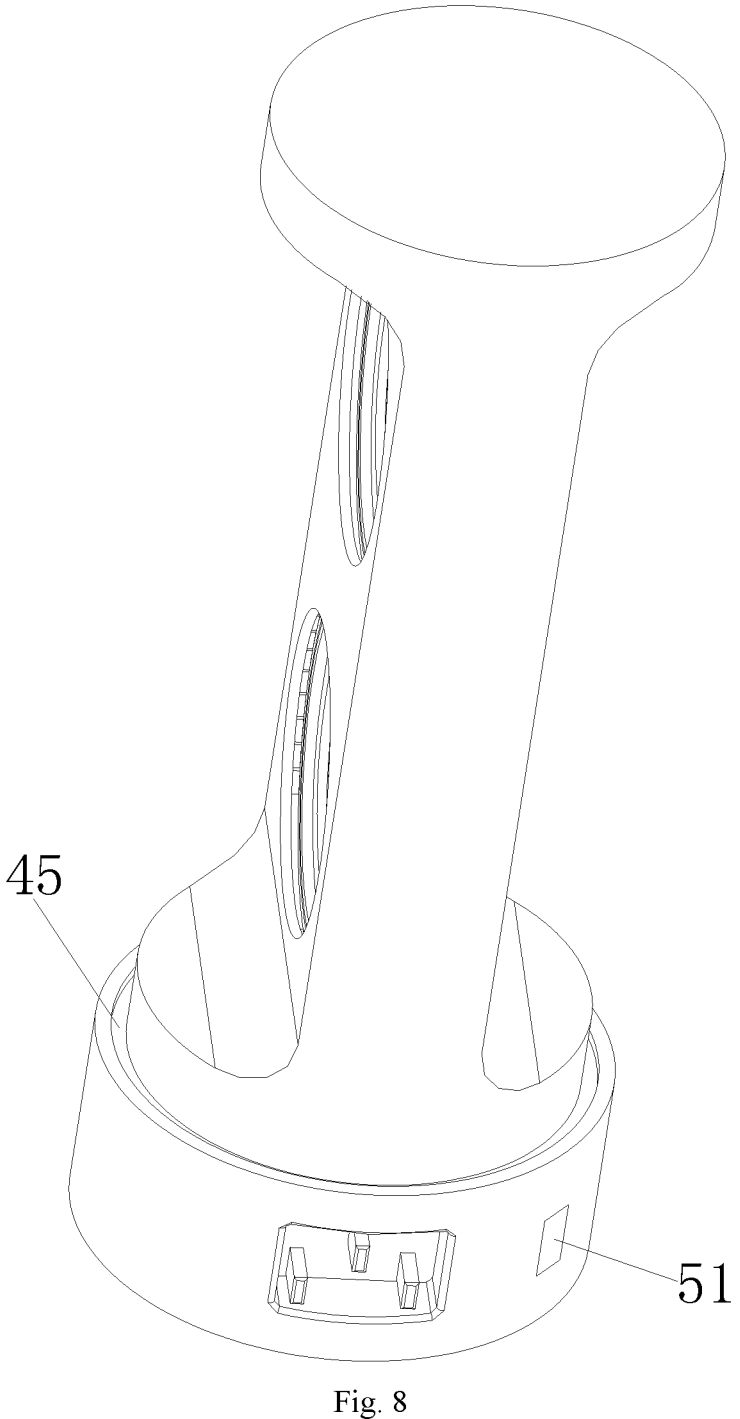
FIG. 8 schematically shows the structure of the storage cylinder according to an embodiment of the present disclosure.
Figure 9:
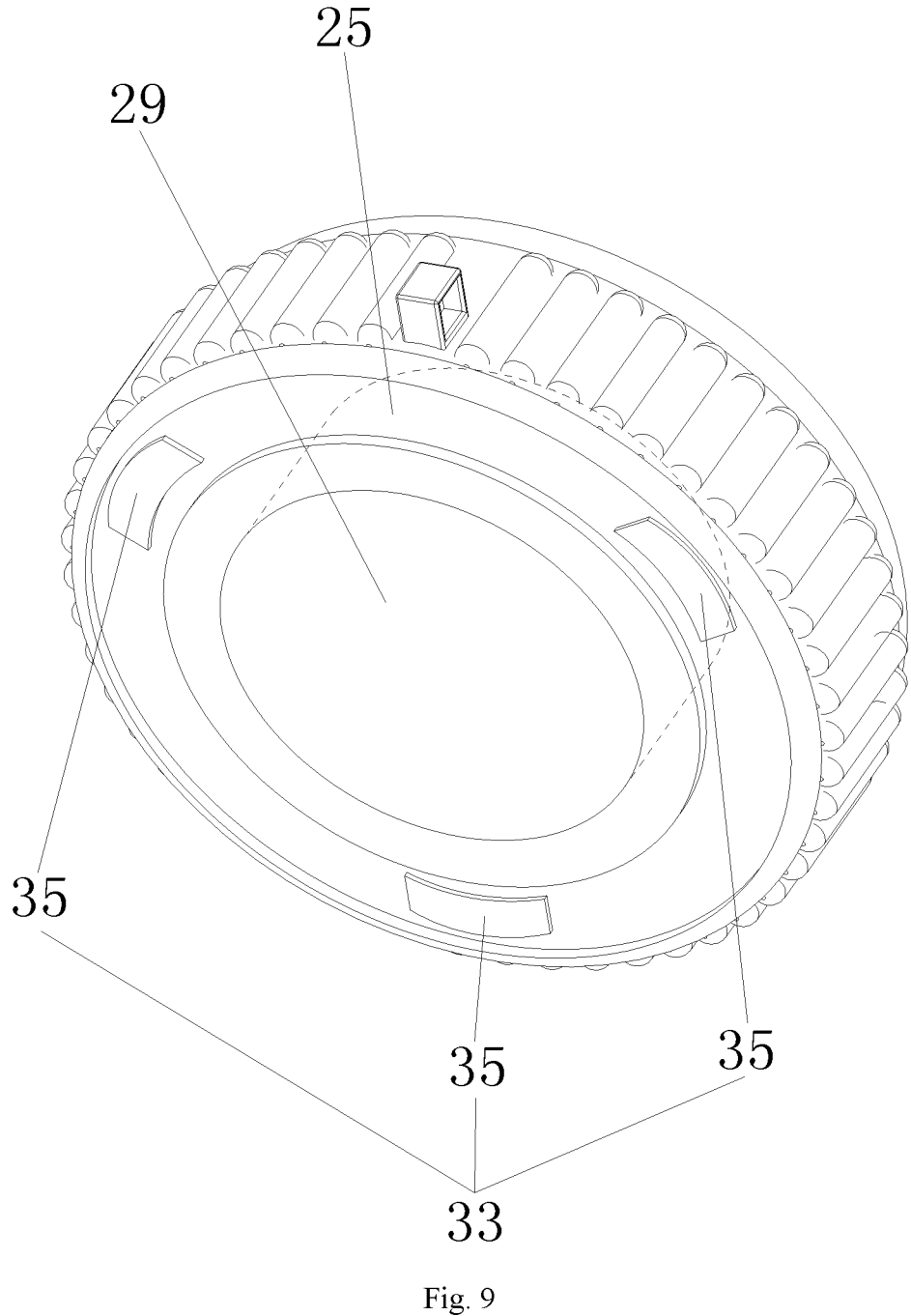
FIG. 9 structurally shows the electronic stethoscope according to an embodiment of the present disclosure in a down-top direction.

Referring to FIGS. 1-9, a stethoscope kit includes a storage cylinder 1, a protective shell 2 and an electronic stethoscope 3. The storage cylinder 1 includes a base 4 and a cylinder body 5. The protective shell 2 is adapted to be sleeved on the cylinder body 5. Two sides of the cylinder body 5 are each symmetrically provided with a recess 6. A bottom of the recess 6 is provided with a accommodating groove 7 configured to accommodate the electronic stethoscope 3. A bottom of the electronic stethoscope 3 is attached to a bottom of the accommodating groove 7 through an attraction mechanism. A charging device 9 is provided in the cylinder body 5. The charging device 9 is configured to charge the electronic stethoscope 3 when the electronic stethoscope 3 is placed in the accommodating groove 7.

In an embodiment, the charging device 9 includes a charging wire 11 and a plurality of engagement devices. The charging wire 11 is provided on the base 4. The plurality of engagement devices are in one-to-one correspondence to accommodating grooves 7. Each of the plurality of engagement devices includes a first drive motor 13, a running channel 14, a rack 15 and an engagement part 16. The running channel 14 includes a first channel 17 and a second channel 18. An accommodating cavity 19 is provided in the cylinder body 5. A first end of the first channel 17 is communicated with the accommodating cavity 19, and a second end of the first channel 17 is communicated with the second channel 18. The second channel 18 is arranged around a side wall of the accommodating groove 7, and the side wall of the accommodating groove 7 is provided with an opening 20 communicated with the second channel 18. The engagement part 16 is electrically connected with the charging wire 11. The engagement part 16 is provided on an end of the rack 15. A side wall of the electronic stethoscope 3 is provided with an engagement block 49. A side wall of the engagement block 49 is provided with an engagement groove 50 configured for insertion of the engagement part 16. The first drive motor 13 is provided on a side of the accommodating cavity 19. An output shaft of the first drive motor 13 is provided with a drive gear 21 configured to be engaged with the rack 15. The engagement part 16 is provided on an end of the rack 15. The first drive motor 13 is configured to drive the rack 15 to move along the running channel 14. The engagement part 16 is located in the first channel 17 in a non-operation state. The first drive motor 13 is configured to drive the drive gear 21 to rotate to move from the first channel 17 to the second channel 18 when the electronic stethoscope 3 is placed in the accommodating groove 7 by a user. Owing to the second channel 18 is placed around the accommodating groove 7, the engagement part 16 will surround a whole circle of the accommodating groove 7. In the circle, the engagement part 16 can be engaged with the engagement block 49 on the electronic stethoscope 3, and it is not needed to rotate the electronic stethoscope 3 by the user, which is very convenient. Similarly, if there is no need to charge or the electronic stethoscope 3 is taken away, the first drive motor 13 is reversed to drive the engagement part 16 to retract into the first channel 17 and the rack 15 to retract into the accommodating cavity 19.

In an embodiment, an interior of the cylinder body 5 is provided with a first control device 22 configured to control the first drive motor 13. The bottom of the accommodating groove 7 is provided with a pressure sensor 23, and the pressure sensor 23 is configured to sense pressure change to determine whether the electronic stethoscope 3 is placed in the accommodating groove 7. The pressure sensor 23 uses an existing flat film pressure sensor 23, and the flat film pressure sensor 23 is configured to sense whether the electronic stethoscope 3 is located in the accommodating groove 7 and send information to the first control device 22.

In an embodiment, the electronic stethoscope 3 includes a case 24, a microphone 25 and a second control device 26. The microphone 25 and the second control device 26 are provided in the case 24. The second control device 26 is provided with a wireless transmission device 27. A top of the case 24 is provided with a start switch 28. A sound-receiving end 29 of the microphone 25 extends out of a bottom of the case 24. An mounting groove 30 is provided from the case 24. A bottom of the mounting groove 30 is provided with a light-emitting diode (LED) 31. The mounting groove 30 is filled with a transparent filling block 32. The start switch 28 is configured to control operation of the second control device 26, and the user can select different sounds of auscultation through pressing the start switch 28. The LED 31 has various lights. When the user selects a breathing sound, a heart sound or a lung sound through the start switch 28 for auscultation, the second control device 26 will control the LED 31 to light corresponding colors for reminding the user.

In an embodiment, the attraction mechanism includes a first magnet group 33 and a second magnet group 34, each including a plurality of magnets 35. The first magnet group 33 is provided on the bottom of the accommodating groove 7. The magnets 35 of the first magnet group 33 are evenly distributed along a circumference of the accommodating groove 7. The bottom of the case 24 is provided with an embedding groove configured embedding of the magnets 35 of the first magnet group 33. The magnets 35 of the second magnet group 34 are evenly distributed along a circumference of the embedding groove. And a magnetic structure used herein is simple.

In an embodiment, a side of the base 4 is provided with a slot 37. A cavity 38 is provided in the base 4. A wire winding device 39 is provided in the cavity 38, and the slot 37 is communicated with the cavity 38 of the base 4. The wire winding device 39 includes a second drive motor 40 and a wire winding reel 44. The charging wire 11 includes a plug 42 and a conductive wire 43. The slot 37 is configured to accommodate the plug 42. The second drive motor 40 is configured to drive the wire winding reel 44 to rotate, so as to wind the conductive wire 43. A side wall of the base 4 is provided with a control button 51, and the control button 51 is configured to control operation of the second drive motor 40. When the stethoscope is in use, the user can take the plug 42 out of the slot 37 and connect the plug 42 to an external power supply. When the stethoscope does not need to be powered, the plug 42 can be disengaged, and then the control button 51 is pressed to make the second drive motor 40 operate, so that the wire winding reel 44 is driven to rotate to wind the conductive wire 43, and the plug 42 will return the slot 37, thereby protecting the plug 42 and allowing for convenient and safe operation.

In an embodiment, the base 4 is provided with an insertion slot 45 around the cylinder body 5. A bottom of the protective shell 2 is provided with a protrusion 46 configured to be inserted into the insertion slot 45, which makes a connection between the protective shell 2 and the base 4 more strong and not easily separate.

In an embodiment, a top of the protective shell 2 is provided with a hole 47. When the user needs to remove the protective shell 2, the user can hold a side wall of an outer of the protective shell 2, and then puts a finger into the hole 47 to press down the cylinder body 5. At the same time, the user can pull the protective shell 2 upward, so that the protective shell 2 can be removed easily, which is very convenient.

Described above are only specific embodiments for illustrating spirits of this application. Various modifications, supplements and replacements made by those skilled in the art without departing from the spirit of this application shall fall within the scope of this application defined by the appended claims.

Though a large number of terms are used herein, it does not exclude the possibility of using other terms. The terms used herein are only for conveniently describing and explaining the nature of the present disclosure, and should not be interpreted as a limitation to this application.

What is claimed is:

1. A stethoscope kit, comprising:
a storage cylinder;
a protective shell; and
an electronic stethoscope;
wherein the storage cylinder comprises a base and a cylinder body; the protective shell is adapted to be sleeved on the cylinder body; two sides of the cylinder body are each symmetrically provided with a recess; a bottom of the recess is provided with an accommodating groove to accommodate the electronic stethoscope; a bottom of the electronic stethoscope is attached to a bottom of the accommodating groove through an attraction mechanism; a charging device is provided in the cylinder body; the charging device is configured to charge the electronic stethoscope when the electronic stethoscope is placed in the accommodating groove; the charging device comprises a charging wire and a plurality of engagement devices; the charging wire is provided on the base; the plurality of engagement devices are in one-to-one correspondence with the accommodating groove; each of the plurality of engagement devices comprises a first drive motor, a running channel, a rack and an engagement part; the running channel comprises a first channel and a second channel; an accommodating cavity is provided in the cylinder body; a first end of the first channel is communicated with the accommodating cavity, and a second end of the first channel is communicated with the second channel; the second channel is arranged around a side wall of the accommodating groove, and the side wall of the accommodating groove is provided with an opening communicated with the second channel; the engagement part is electrically connected with the charging wire; the engagement part is provided on an end of the rack; a side wall of the electronic stethoscope is provided with an engagement block; a side wall of the engagement block is provided with an engagement groove configured for insertion of the engagement part; the first drive motor is provided on a side of the accommodating cavity; an output shaft of the first drive motor is provided with a drive gear configured to be engaged with the rack; the first drive motor is configured to drive the rack to move along the running channel; the engagement part is located in the first channel in a non-operation state; an interior of the cylinder body is provided with a first control device configured to control the first drive motor; and the bottom of the accommodating groove is provided with a pressure sensor, and the pressure sensor is configured to sense pressure change to determine whether the electronic stethoscope is placed in the accommodating groove.

2. The stethoscope kit of claim 1, wherein the electronic stethoscope comprises a case, a microphone and a second control device; the microphone and the second control device are provided in the case; the second control device is provided with a wireless transmission device; a top of the case is provided with a start switch; a sound-receiving end of the microphone extends out of a bottom of the case; the top of the case is provided with a mounting groove; a bottom of the mounting groove is provided with a light-emitting diode (LED); and the mounting groove is filled with a transparent filling block.

3. The stethoscope kit of claim 2, wherein the attraction mechanism comprises a first magnet group and a second magnet group; the first magnet group comprises a plurality of first magnets, and the second magnet group comprises a plurality of second magnets; the first magnet group is provided on the bottom of the accommodating groove; the plurality of first magnets are evenly distributed along a circumference of the accommodating groove; the bottom of the case is provided with an embedding groove configured for embedding of the plurality of first magnets; and the plurality of second magnets are evenly distributed along a circumference of the embedding groove.

4. The stethoscope kit of claim 2, wherein a side of the base is provided with a slot; a cavity is provided in the base; a wire winding device is provided in the cavity; the slot is communicated with the cavity of the base; the wire winding device comprises a second drive motor and a wire winding reel; the charging wire comprises a plug and a conductive wire; the slot is configured to accommodate the plug; the second drive motor is configured to drive the wire winding reel to rotate, so as to wind the conductive wire; and a side wall of the base is provided with a control button, and the control button is configured to control operation of the second drive motor.

5. The stethoscope kit of claim 1, wherein the base is provided with an insertion slot around the cylinder body; and a bottom of the protective shell is provided with a protrusion configured to be inserted into the insertion slot.

6. The stethoscope kit of claim 1, wherein a top of the protective shell is provided with a hole.

* * * * *